United States Patent [19]

Hartl et al.

[11] 4,394,452

[45] Jul. 19, 1983

[54] SYNTHETIC STOOL

[75] Inventors: Roland Hartl, Eppertshausen; Dieter Helm, Heppenheim, both of Fed. Rep. of Germany

[73] Assignee: Röhm GmbH, Darmstadt, Fed. Rep. of Germany

[21] Appl. No.: 910,285

[22] Filed: May 30, 1978

[30] Foreign Application Priority Data

May 31, 1977 [DE] Fed. Rep. of Germany ....... 2724438
May 2, 1978 [DE] Fed. Rep. of Germany ....... 2819284

[51] Int. Cl.³ .................. G01N 33/72; C09K 3/00
[52] U.S. Cl. .................................... 436/66; 106/126; 106/128; 106/193 D; 106/193 J; 272/8 N; 434/267; 436/15; 436/16; 524/430; 524/560; 524/606
[58] Field of Search ............... 23/230 B, 253 TP, 931; 252/408; 106/162, 163 R, 126, 128, 193 J, 193 D, 137, 316, 288 B, 288 Q; 260/29.2 N; 434/262, 267, 272; 272/1 R, 8 R, 8 N, 27 R, 27 N; 436/15, 16, 66; 524/430, 560, 606

[56] References Cited

U.S. PATENT DOCUMENTS

| | | | |
|---|---|---|---|
| 1,600,599 | 9/1926 | Parker | 434/272 |
| 2,320,098 | 5/1943 | Quisling | 106/126 X |
| 2,699,401 | 1/1955 | Grossi | 106/193 J |
| 2,799,660 | 7/1957 | Nicholls et al. | 23/931 X |
| 2,925,365 | 2/1960 | Nicholson et al. | 106/137 X |
| 3,427,176 | 2/1969 | Moriya | 106/193 D X |
| 3,996,006 | 12/1976 | Pagano | 422/58 X |

FOREIGN PATENT DOCUMENTS 432571 7/1935 United Kingdom ............... 106/126

OTHER PUBLICATIONS

Johnson Smith Company, Catalog of Surprising Novelties for Fun Lovers, p. 56.

*Primary Examiner*—Arnold Turk
*Attorney, Agent, or Firm*—Curtis, Morris & Safford

[57] ABSTRACT

Synthetic stool, adaptable to use as a control standard in the diagnostic detection of substances contained in stools and for demonstration purposes, said stool comprising a matrix of a member selected from the group consisting of oxygen-containing organic polymers which are difficultly soluble in water and oxygen-containing inorganic solids difficultly soluble in water, a non-bleeding coloring agent adherent to said matrix and simulating the color of a stool, and a liquid selected from the group consisting of water and lubricants.

2 Claims, No Drawings

SYNTHETIC STOOL

The present invention relates to a synthetic stool and to methods of making and using the same.

Examination of the stool offers a diagnostic possibility that has been exploited in the past in medicine but which has received new topicality because of the development of modern analytical methods.

Macroscopic examination gives information on the digestive functioning; the consistency and form of the stool are indicators of sicknesses such as pancreatic insufficiency, steatorrhea, stomach or intestinal bleeding, colonic spasms, dyspepsia, and infectious diseases such as dysentery, inter alia (cf. "Klinisches Labor", 11th ed. of Medizinischchemischen Untersuchungsmethoden, p. 474, published by E. Merck, Darmstadt 1970).

Microscopic examination can provide further information of diagnostic value, for example of the presence of fat and muscle protein in the stool. Further, a determination of the content of certain enzymes, parasites, bacteria, drugs, etc., is included in the scope of the examination.

However, examination of the stool for occult blood is of particular significance. The problem to be solved by the present invention and the different possibilities laid open by the invention from the point of view of diagnosis, examination, and demonstration will be illustrated by reference to this method.

Tumorous diseases in the intestinal region are relatively common. They make themselves evident at a late stage—often at too late a stage for the patient. One indicium of the presence of tumors in the intestinal region—although it is not a completely unambiguous one—is the appearance of blood in the stool. However, the presence of blood in the stool is not often perceived macroscopically, above all if the blood is present in the stool only in traces and if the stool is of a dark color. Thus, the development of a process with the aid of which even minimal amounts of blood could be diagnosed in the stool without error would represent a significant advance in the recognition of tumors in the intestinal region. Of course it is understood that a prerequisite is that a meatless diet be observed for about three days prior to carrying out the test. The test involves the determination of the hemoglobin component of blood, more precisely the detection of the peroxidase activity inherent in hemoglobin. For example, if peroxide is simultaneously present, hemoglobin acts on the components of guaicum resin to produce a clearly recognizable blue to blue-green color.

In a similar way, other reagents can also be employed to detect the presence of hemoglobin by changes in color, for example benzidine, o-tolodine (dimethylbenzidine), tetramethylbenzidine, and phenolphthalein, inter alia.

Such tests are carried out with impregnated paper strips or coated film strips and are generally designated as "test strip methods".

In practice, the test is usually carried out by first placing small stool samples onto designated portions of a small test leaflet impregnated with a solution of guaicum resin. Then, one or two drops of a hydrogen peroxide solution are added to the test sheet as a "developer". If blood is present then the described blue to blue-green color appears.

Clinical experiments have shown that up to about two ml. of blood in 100 g of feces could be detected with certainty if the stool samples on the test sheet were dry. However, if the developer solution was used immediately after the application of the stool sample to the test leaflet, that is with the sample in a moist condition, then the limit of detectability decreased to about four ml. of blood in 100 g. of feces.

The above described diagnostic test is designated hereinafter as the "guaicum test method".

In the interest of diagnostic reliability of the test technique, the reagents used and the finished test leaflet must be submitted to a (statistical) quality control before they can be given to the patient.

Further, the doctors and medical-technical assistants who work with this diagnostic method should have an opportunity continually to supervise the test method. Finally, it would be very advantageous to be able to demonstrate the test method.

The possibilities for checking the test leaflets under practising conditions and for demonstrating a positive result with the test method were heretofore limited. If undiluted blood is applied for test purposes to the filter paper of a test leaflet prepared in the above-described manner, the blood cells may possibly not be hemolyzed. Thus, no peroxidase is released and it is possible that the guaicum reaction will behave atypically. Even if care is taken that the blood is hemolyzed, such a test check with blood does not come very close to the conditions which prevail when the test is carried out in practice.

Such a check would be of much more significant predictive value if a postive indication of blood could be demonstrated at the lower limit of detection. Carrying out the test with (hemolyzed) blood is also badly adaptable to demonstrating the method. The first step toward duplicating practical conditions involves the addition of a (predetermined) amount of blood to a given stool sample, the blood content of which is not known in advance. In order to make any judgment on the quality of the test leaflet, an amount of blood must be added to the stool sample which is above the usual limit of detection. If the reaction is positive, however, the reliability of the test leaflet would then be confirmed without question only if it could be determined by a parallel experiment that the stool sample before the addition of blood (control sample) produced a negative result, that is, was free of blood. If the control sample which has not been combined with blood conforms in this way, then it should be guaranteed that no error of whatever sort is involved either with the test leaflet or in handling. For this purpose one would most likely have to submit one of the first of various stool samples to the test. But an absolute certainty that the test leaflet possesses a detection sensitivity according to specifications also cannot be achieved by this method. The problems of such a quality control are clear from the following facts: Even normal persons lose about 0.5–1.5 ml. of blood into the stool in 24 hours. If it is now taken into consideration that the daily production of stool can vary from individual to individual between 100 g. and 500 g., it is clear that it is not possible to define anything like a natural "standard stool" in the clinical-chemical sense.

That the handling of stools in the context of health care should be kept to the absolutely necessary minimum for reasons of hygiene requires no particular explanation.

It can be asserted that the diagnostic possibilities which are offered by stool examination are not generally fully exploited because of the inconvenience and risks involved. The difficulties begin even with demonstrating the kind of stool typical for a particular diagnostic condition or with demonstrating the analytical method.

In tests for occult blood, the adjustment of a natural sample to a predetermined blood content is practically impossible since, as mentioned earlier, varying amounts of blood are contained in the stool of very healthy, normal persons.

It has been found that a synthetic stool fills the need for a synthetic substitute for the common types of natural stools in an outstanding manner. Such a synthetic stool consists of a matrix comprising at least one oxygen-containing organic polymer which is difficultly soluble in water and/or a difficultly soluble oxygen-containing inorganic solid body, at least one non-bleeding dyestuff adhering to the matrix which is capable of producing color similar to that of a stool, water and/or a lubricant, and, optionally, a preserving agent. In particular, the synthetic stool according to the present invention is suitable as a control standard in the detection of blood in the stool according to the test-strip method, especially according to the guaicum color test.

As oxygen-containing organic polymers which are difficultly soluble in water and which are suitable as the matrix material, the following come into consideration:

(A) cellulose and chemically-modified cellulose derivatives and/or other carbohydrates;

(B) proteins such as gelatin, preferred for the partial replacement of carbohydrate materials according to (A);

(C) synthetic polyamides obtained by condensation polymerization, such as polyhexamethylene adipamide (PA 6.6); and (D) polymers of acrylic and methacrylic compounds having a hydrophilic functional group therein, such as polymers of acrylic acid, methacrylic acid, their salts, their amides (such polyamides are addition polymers), their hydroxyalkyl esters, and their dialkylaminoalkyl esters, for example polymers of the type found in commercially-available ion exchangers or matrices used in gel chromatography [cf. H. Rauch-Puntigam and T. Voelker "Acryl-und Methacrylverbindungen", Springer-Verlag, Berlin (1967), incorporated herein by reference].

As oxygen-containing, difficultly-soluble inorganic solid bodies, aluminum oxide can be mentioned by way of example. Also, mixtures of various components of the type described above give useful matrices.

In order to achieve a consistency as closely similar as possible to that of a natural stool, predominantly granular matrix materials and coloring pigments having a grain size of about 300 microns, preferably in the region from 0.5 to 50 microns, are suitably used. Of course, the presence of entities of a larger structure, as in a natural stool, should not impair their use.

Using the above-described basic components, substitutes for types of stools which are normally encountered and which are encountered under pathological conditions can be prepared according to the invention. For example, the amounts of liquids such as water, preservative, and/or lubricant is chosen according to the kind of stool which is to be prepared. The amount naturally depends also on the ability of the matrix material to absorb and bind water. In general, the moisture content is so chosen that the material can be handled with a spatula.

In case carbohydrates according to (A) are used as the matrix material, the amount of liquid can be up to about 55% by weight of the total preparation, for example, of which the predominant amount, for example up to about 45% by weight, is water, 5–15% by weight may be a lubricant, especially glycerin or polyethyleneglycol, and the remaining may be, for example, alcohols (ethanol). These proportions are valid also if there is a partial replacement of carbohydrate material by, for example, a protein such as gelatin according to (B).

If polyamides are used according to (C), a relatively high content of lubricants is used, for example glycerin in an amount which is 5-fold to 7-fold the weight of polyamide.

Likewise when acrylic or methacrylic derivatives such as polyacrylamide are used, a relatively high content of liquid, for example 5-fold to 20 fold, preferably about 18-fold, the weight of solid resin is suitable. In this case, lubricants can be employed together with water, preferably in a weight ratio of 1:1 to 1:1.5.

Also when aluminum oxide is used as the oxygen-containing difficultly-soluble inorganic matrix, a liquid addition which is 2-fold to 5-fold, preferably about 2.3 fold, by weight, is suitable. As a rule, a considerable excess of lubricant, about a 12-fold to 18-fold excess, preferably a 15-fold excess, by weight with respect to water, is to be recommended. As lubricants, polyalcohols such as glycerin and/or polyethylene glycol ("Polywax 6000") principally come into consideration, optionally with the addition of monoalcohols such as ethanol.

As preservatives, the preserving agents permitted for use with foodstuffs are suitably employed, particularly solid preservatives such as sodium benzoate, benzoic acid, or sorbic acid. However, the addition of ethanol may also have a preserving action, for example. The amount of preservatives depends on the efficacy of the preservative in question, which may, for example, be known from their use as preservatives for foodstuffs. In general, an amount of 3 percent by weight is not exceeded and the amount as a rule is between 0.1 and 2% by weight of the total preparation.

By definition, it is required of the coloring agents employed according to the invention that they adhere to the matrix, do not bleed, and together with the matrix, produce a lasting coloring effect which is as close as possible to that of a natural stool. The requirement for adherence can be satisfied, for example, if the coloring agent or agents undergo bonding with the matrix, for example, in the manner of reactive dyestuffs, or if the matrix can be thoroughly mixed with at least one insoluble coloring agent, whereupon adherence is produced in a physical manner and bleeding is similarly avoided.

The choice of colorant will thus take into consideration the nature of the matrix and the nature and degree of the—as a rule known—susceptibility of the matrix material to coloring by colorants. When choosing a colorant, it must also be taken into consideration that, on treatment with a hydrogen peroxide solution as a "developer", no interfering change in color or no change in color which can be mistaken for a positive color reaction in the guaicum test is permitted to occur.

In addition, the coloring agent which is formed in the test should not itself be bonded by the matrix.

The following materials are mentioned as coloring agents:

(A) a group of yellowish to brownish pigments, for example a mixture comprising iron oxides respectively having a brown and yellow tone, preferably in a weight ratio of 3:2, or, for example, mixed phase pigments comprising iron and chromium oxide, for example, chromium iron brown (Color Index 1: pigment brown 29; Index 2: No. 77-500):

(B) organic dyes which undergo bonding to the matrix, in particular reactive dyes, for example those which contain unsaturated heterologous residues including reative halogen, such as pyrimidine, chlortriazine, chlorpyrazine and chlorpyrimidine, in which the halogen reacts with OH— or $NH_2$— groups in the substrate which is to be colored [substitution dyes cf. Textilveredlung 7, 297, (1972)]; or those dyes which contain a $-SO_2-(CH_2)_2-OSO_3Na$ group as the color-imparting group, for which the vinyl sulfone group which is formed reacts with OH— or $NH_2$— groups of the substrate to be colored [addition dyes, cf. Dtsch. Faerber-Kat. 79, 188 (1975)], for example a combination of the dye Remazol-Red B (Reactive Red 22=C.I. 14 824), Remazol-Golden Yellow G (Reactive Yellow 17=C.I. 18 852), and Remazol-Brilliant Blue R (Reactive Blue 19=C.I. 61 200), preferably in a weight ratio of 2:2:1; and (C) suitable finely-divisible, preferably powdered, materials comprising natural products having a yellow-to-brown coloration, for example commercial powdered cocoa.

Coloring can occur in the course of mixing the components of the final preparation or, particularly when using a colorant according to (B) above, can occur earlier by a separate coloring of the matrix material or of one of its components.

A preferred embodiment of the synthetic stool according to the invention which has proved particularly suitable as a control standard in the diagnostic determination of blood in the stool according to the test strip method is obtained using cellulose, modified cellulose and other carbohydrates, lubricants, and the aforementioned coloring agents, preservatives, and water. A preparation containing between about 30-35% by weight of cellulose (preferably about 33% by weight of cellulose, and about 0.3-1.2% by weight of modified, preferably water-soluble cellulose), 0.5-1.2% by weight of other water-binding carbohydrates (preferably cross-linked dextrans), between 5 and 10% by weight of lubricant (preferably about 7.5% by weight of glycerin or of polyethylene glycol) 1.2% by weight of coloring agents which are suitable to produce a color similar to that of a natural stool, preferably 1.5-3% by weight of a preservative (preferably about 0.5 to 1% by weight of ethanol and about 0.1 to 2% by weight of a solid preservative— preferably about 1.5% by weight of sodium benzoate, benzoic acid, or sorbic acid), and water to give 100% is particularly preferred.

As the cellulose component, microcrystalline cellulose is preferably employed. As the modified cellulose, low molecular weight water-soluble cellulose ethers like methylhydroxyethyl cellulose are preferred. As cross-linked dextrans, preferably three dimensionally cross-linked swellable dextrans are employed such as those used as matrices in gel chromatography. As dyestuffs which are suitable to produce a color similar to that of a stool, those pigments mentioned above under (A) are preferably used, for example colorants comprising iron oxides having brown and yellow color tones in a weight ratio of 3:2, or the reactive coloring agents mentioned under (B) are used.

From the point of view of suitability of the preparations according to the present invention as a control standard in the detection of occult blood according to the test strip method, particular attention must be paid to the following:

When using pure cellulose-water-iron oxide-mixtures, spreadability is unsatisfactory. The filter paper absorbs the moisture from the synthetic stool too rapidly and a smear can be prepared with the synthetic stool only with difficulty.

The low molecular weight water-soluble cellulose ethers of the methylhydroxyethyl cellulose type are suitable for thickening the synthetic stool and considerably increase their spreadability without impairing the color reaction. A synthetic stool according to the present invention develops a paste-like consistency upon addition of the aforementioned cellulose ethers.

High molecular weight cellulose ethers would push the limit of detection in the guaicum test to higher blood concentrations. Also a higher concentration of water-soluble cellulose ethers has a similar effect.

The addition of glycerin, on the one hand, favorably influences spreadability. On the other hand, glycerin imparts to the mass a slightly shiny appearance similar to that of a natural stool. The addition of cross-linked dextrans improves the storability of the synthetic stool by the binding of excess water such that after three-weeks' storage in tubes little tendency for the formation of a watery-runny consistency is observed.

A better understanding of the present invention and of its many advantages will be had by referring to the following specific examples, given by way of illustration.

EXAMPLE 1

5.5 g. of low molecular weight water-soluble methyl-hydroxyethyl cellulose ("Tylose MH 20") having a maximum particle size of 200 microns are made into a slurry with 9.8 g. of undenatured ethanol. After the addition of 540 g. of water, the mixture is stirred for 15 minutes and thereafter 10.0 g. of cross-linked dextran suitable for use as an ion exchanger ("Sephadex G 25") having a maximum particle size of 63 microns are added. Fifteen minutes later, 14.5 g. of powdered sodium benzoate and 73.1 g. of glycerin are added. The whole is then stirred or shaken for three hours.

(If a stock solution is prepared, it should be noted that "Sephadex G 25" settles with time. Shake before using.)

333 g. of microcrystalline cellulose ("Avicel"), having a maximum particle size of 40 microns, 9.0 g. of powdered iron oxide brown, and 6.0 g. of iron oxide yellow having a maximum particle size of 40 microns are thoroughly mixed in a dry state. The previously-prepared, somewhat cloudy solution is added hereto and both are mixed. After standing for one hour, the synthetic stool is mixed together well once more.

EXAMPLE 2

Standard stool containing 0.4% by weight of blood

Human blood (preserved blood) is diluted with water in a volume ratio of 1:3 and permitted to stand for three hours. 240 microliters of the diluted blood are added to 20 g. of synthetic stool prepared according to Example 1 and the whole is mixed well. Thereafter the mixture is left to stand about one hour and then mixed thoroughly again. This standard stool containing about 0.4% of blood should be used within 24 hours.

EXAMPLE 3

Preparation of synthetic stool for packing in tubes 0.52 g. of low molecular weight water-soluble methylhydroxyethyl cellulose ("Tylose MH 20") are combined with 51 ml. of water and left to stand for 24 hours with stirring from time to time. 12 g. of glycerin and 1.5 g. of sodium benzoate are added thereto. The solution so obtained is added to 27 g. of microcrystalline cellulose ("Avicel PH 101") having a maximum particle size of 63 microns which was earlier thoroughly mixed with 0.8 g. of iron oxide brown and 0.4 g. of iron oxide yellow. The mixture, which has a pliant consistency, is stirred. Human blood diluted 1:3 can be added to this mixture in an amount of 1.5%. The stool so obtained is outstandingly suitable for packing in tubes.

EXAMPLE 4

This embodiment is similar to that in Example 1 with the exception that 5 g. of gelatin (white, extra fine) are employed instead of the soluble methylhydroxyethyl cellulose.

EXAMPLE 5

This embodiment is like that in Example 1 except that 73.1 g. of water-soluble polyethylene glycol ("Polywax 6000") having a particle size of 2 to 3 millimeters is used instead of glycerine.

EXAMPLE 6

This embodiment is the same as that in Examples 1 to 3 with the exception that the iron oxide pigment is replaced by a reactive coloring agent bound to dextran. The colored dextran component can be prepared by mixing 20 g. of dextran having a maximum particle size of 250 microns and a dye mixture comprising 100 mg. of Remazol-Brilliant Blue (C.I. 61 200), 200 mg. of Remazol-Red B (C.I. 14 824), and 200 mg. of Remazol-Golden Yellow (C.I. 18 852) in 200 ml. of distilled water and, after adjustment of the pH value to 12.0, incubating the mixture for 16 hours at room temperature. At the end of the incubation, precipitation is carried out with ethanol and the precipitate is washed several times. The product is brown-colored after drying.

EXAMPLE 7

A synthetic stool comprising colored cellulose

Microcrystalline cellulose ("Avicel") is tinted brown as in Example 6.

2 g. of the colored microcrystalline cellulose are mixed with 3.6 g of glycerin. A dark brown product having satisfactory spreadability is obtained.

EXAMPLE 8

A synthetic stool comprising colored dextran

Cross-linked dextran for use as an ion exchanger ("Sephadex G 25") is colored as in Example 6.

A synthetic stool having a bright color is obtained as in Example 1 from the components mentioned therein except that the colored dextran is used without addition of pigment and that the microcrystalline cellulose (300 g. instead of 333 g.) is added at the beginning.

EXAMPLE 9

A synthetic stool comprising colored polyamide

Polyamide 66 having a particle size of 40 microns is colored brown as in Example 6 with Remazol dyes. 2.5 g. of colored polyamide are mixed with 15.0 g. of glycerin. A product of good stability and optimum spreadability is obtained.

EXAMPLE 10

A synthetic stool comprising polyacrylamide and iron oxide pigments 2.5 g. of polyacrylamide ("Biogel P 150") having a maximum particle size of 90 microns are mixed with 20.0 g. of glycerin and 25.0 g. of distilled water with the addition of 0.9 g. of iron oxide brown and 0.6 iron oxide yellow. The synthetic stool is suitable for demonstration purposes but shows only moderate spreadability because of the swollen particles.

EXAMPLE 11

A synthetic stool comprising polyamide and dextran colored with reactive dyes

This embodiment can be prepared as in Example 10 but with the addition of 1.5 g. of dextran, colored as in Example 6, instead of the iron oxide pigment.

EXAMPLE 12

A synthetic stool comprising aluminum oxide and iron oxide colors 14.0 g. of aluminum oxide ("Martoxin") having a maximum particle of 40 microns are mixed with 2.0 g. of distilled water and 30.0 g. of glycerin with the addition of 0.9 g. of iron oxide brown and 6 g. of iron oxide yellow. The synthetic stool has a relatively liquid adhesive consistency.

EXAMPLE 13

A synthetic stool comprising cellulose with cocoa powder as the colorant 20 g. of a microcrystalline cellulose used in thin-layer chromatography (Merck) are combined with 20 g. of powdered cocoa and 200 ml. of distilled water. The mixture is kept overnight in a rolling mill. Subsequently, the material is filtered on a frit and washed with water. 7.0 g. of the damp product are mixed with 5 g. of glycerin.

USE OF THE PREPARATION ACCORDING TO EXAMPLES 1-13

By the addition of about 1.5% by weight of blood to the preparations of Examples 1-13, a high-quality control standard for use in the diagnostic detection of blood in the stool according to the test strip method, particularly the guaicum-color test, is generally obtained.

The detection sensitivity for blood in a synthetic stool according to Example 1 is at a blood content of 0.4% by weight when using commercially-available test leaflets.

The limit of detection of blood in a natural stool is, under otherwise similar conditions, at about 1.2–1.6% by weight of blood. The limit of detection of blood in the synthetic stool according to the present invention is, thus, lower than for blood in a natural stool. Thus, an essential prerequisite for using the synthetic stool according to the present invention for control purposes is met. The freshly prepared standard stool according to Example 2 is thus suitable for checking test leaflets, for example.

What is claimed is:

1. A synthetic human stool, spreadable on a substrate and adaptable to use as a control standard in the diagnostic detection of occult blood in the stool, said synthetic stool consisting essentially of a matrix of a member selected from the group consisting of oxygen-containing organic polymers which are difficultly soluble in water and oxygen-containing inorganic solids difficultly soluble in water, a non-bleeding coloring agent adherent to said matrix and simulating the color of a human stool, a liquid selected from the group consisting of water and lubricants, and a predetermined amount of hemolyzed human blood, said coloring agent on treatment with hydrogen peroxide showing no change in color or no change in color interfering with such a diagnostic detection of occult blood.

2. The method of checking, standardizing, or comparison testing a diagnostic test strip for the detection of blood in the stool which comprises applying a test quantity of a synthetic stool as in claim 1 to said test strip, applying hydrogen peroxide to the test strip, and observing a detectable response.

* * * * *